United States Patent [19]

Kagiya et al.

[11] Patent Number: 4,977,273
[45] Date of Patent: Dec. 11, 1990

[54] FLUORINE-CONTAINING 2-NITROIMIDAZOLE DERIVATIVES

[75] Inventors: Tsutomu Kagiya; Mitsuyuki Abe, both of Kyoto; Seiichi Nishimoto, Nara; Yuta Shibamoto, Kyoto; Susumu Otomo, Kounosu; Tohru Tanami, Tokyo; Kazuhiro Shimokawa, Settsu; Toru Yoshizawa, Osaka; Yorisato Hisanaga, Ibaraki, all of Japan

[73] Assignees: Kyoto University of Honmachi, Kyoto; Taisho Pharmaceutical Co., Ltd., Tokyo; Daikin Industries, Ltd., Osaka, all of Japan

[21] Appl. No.: 448,909

[22] Filed: Dec. 12, 1989

[30] Foreign Application Priority Data

Dec. 14, 1988 [JP] Japan .................. 63-315974

[51] Int. Cl.$^5$ .......................... C07D 233/91
[52] U.S. Cl. .................................. 548/339
[58] Field of Search .......................... 548/339

[56] References Cited

FOREIGN PATENT DOCUMENTS 294847 12/1988 European Pat. Off. ............ 548/339

OTHER PUBLICATIONS

Chemical Abstracts, vol. 107, Aug. 31, 1987, No. 9, Abstract 73465t; C. J. Mathias et al.
(List continued on next page.)

Primary Examiner—John M. Ford
Assistant Examiner—Robert C. Whittenbaugh
Attorney, Agent, or Firm—Birch, Stewart, Kolasch & Birch

[57] ABSTRACT

A 2-nitroimidazole derivative of the formula:

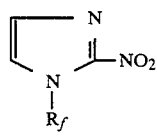

(I)

wherein $R_f$ is a group of the following formula (II) or (III):

$$-CH_2CFXCH_2OR_1 \qquad (II)$$

wherein X is a hydrogen atom or a halogen atom; $R_1$ is a group of the formula:

$$-CH_2CH-OR_2$$
$$\quad\quad\;\; |$$
$$\quad\quad\;\; CH_2OR_2$$

$$-CH(CH_2OR_2)_2$$

$$-(CH_2)_lOR_2$$

$$-(CH_2)_lCOR_2 \text{ or}$$

$$-(CH_2)_m(CF_2)_n[CONH(\overset{R_3}{\underset{|}{CH}})_o(CF_2)_p]_qZ$$

wherein $R_2$ is a hydrogen atom, a hydroxyl group, a $C_1$-$C_3$ alkyl group, a $C_2$-$C_4$ acyl group, benzylidene or acetonide; $R_3$ is a hydrogen atom or a $C_1$-$C_3$ alkyl group; Z is a hydrogen atom, COOY, COOR$_3$, CONHOY, CONR$_4$R$_5$ (wherein R$_4$ and R$_5$ are hydroxyl group-containing $C_1$-$C_3$ alkyl groups or hydrogen atoms; Y is a hydrogen atom or a monovalent metal atom), an amino group, a hydroxyl group or OR$_3$; l is an integer of 1 to 3; o is an integer of 0 to 3; p is an integer of 0 to 2; q is an integer of 0 to 3; m and n are integers of 0 to 4; and $1 \leq m+n \leq 4$ or $$-CH_2(CX_2)_s[CONH(\overset{R_3}{\underset{|}{CH}})_t(CF_2)_p]_rZ' \qquad (III)$$

wherein R$_3$, X and p are the same as defined above; Z' is the same as Z or is OCOOCH$_3$; r is an integer of 1 to 3; s is 0 or 1; t is an integer of 0 to 4 provided that when p=0, s≠0 and at least one X is a fluorine atom; and a radiosensitizer comprising said nitroimidazole derivative.

1 Claim, 1 Drawing Sheet

OTHER PUBLICATIONS

Chemical Abstracts, vol. 89, Dec. 4, 1978, No. 23, Abstract 191005a; A. M. Rauth et al.

Chemical Abstracts, vol. 89, Dec. 4, 1978, No. 23, Abstract 191006b; J. M. Brown et al.

Chemical Abstracts, vol. 89, Chemical Substance Index, I-PO, p. 2720cs.

Chemical Abstracts, vol. 105, No. 18, Nov. 3, 1986; Abstract No. 160447r; P. A. Jerabek et al.

Chemical Abstracts, vol. 105, Oct. 13, 1986, No. 15, Abstract No. 130194p; J. A. Raleigh et al.

FLUORINE-CONTAINING 2-NITROIMIDAZOLE DERIVATIVES

BACKGROUND OF THE INVENTION

1. Field of the Invention

The present invention relates to novel fluorine-containing 2-nitroimidazole derivatives and a radiosensitizer comprising the same, which facilitates inactivation of intractable hypoxic cells in malignant tumors by irradiation.

2. Description of the Related Art

To suppress reproduction or growth of malignant tumor cells, radiation exposure and administration of anti-tumor compounds or immunity substances are known and actually employed independently or in combination with surgical therapy. Among them, the radiation exposure has been employed for a long time.

A hypoxic cell sensitizer (or radiosensitizer) which is a drug for increasing sensitivity of the hypoxic cells against the radiation has been developed since it is promising means for increasing effects of radiotherapy.

Hitherto, various hypoxic cell sensitizers have been developed (cf. "Gan to Kagakuryoho" (Cancers and chemotherapy), Vol. 8, No. 11, November 1981, 1659).

1-(2-Nitro-1-imidazolyl)-3-methoxy-2-propanol (Misonidazole), which is one of typical hypoxic cell sensitizers, is about twice as effective as when no Misonidazole is used. However, it is hardly administered in an effective amount since it has strong neurotoxicity. No sensitizing effect was confirmed from the results obtained by administering it in human beings (cf. Reference 4 cited in the above "Gan to Kagakuryoho").

To increase sensitizing activity of the radiation and simultaneously to decrease the neurotoxicity, nitroimidazole derivatives have been studied (cf. Japanese Patent Kokai Publication No. 12763/1987). However, the conventional derivatives have insufficient radiosensitization It has been found that the radiosensitizing function of the azole compounds is attributed to their azole rings while the side chain contributes to their solubility in oils and pharmacological characteristics (Int. J. Radiat. Biol., 35, 1979, 151).

Compounds having a fluorine atom at a specific position in a molecule have been increasingly used as medicines because of mimic effects of the fluorine atom or modification of methabolic inhibition effect and solubility in oils (cf. "Kagaku no Ryoiki" (Chemical Fields), 35, 441 (1981)).

SUMMARY OF THE INVENTION

One object of the present invention is to provide a novel fluorine-containing nitroimidazole derivative having a fluorinated substituent on its imidazole ring.

Another object of the present invention is to provide a fluorine-containing radiosensitizer which increases sensitivity of the hypoxic cells against radiation but has improved pharmacological characteristics and low toxicity and neurotoxicity.

Accordingly, the present invention provides a 2-nitroimidazole derivative of the formula:

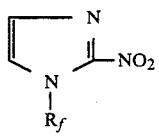  (I)

wherein $R_f$ is a fluorine-containing organic group and a radiosensitizer comprising said nitroimidazole derivative.

DETAILED DESCRIPTION OF THE INVENTION

Figure 1:
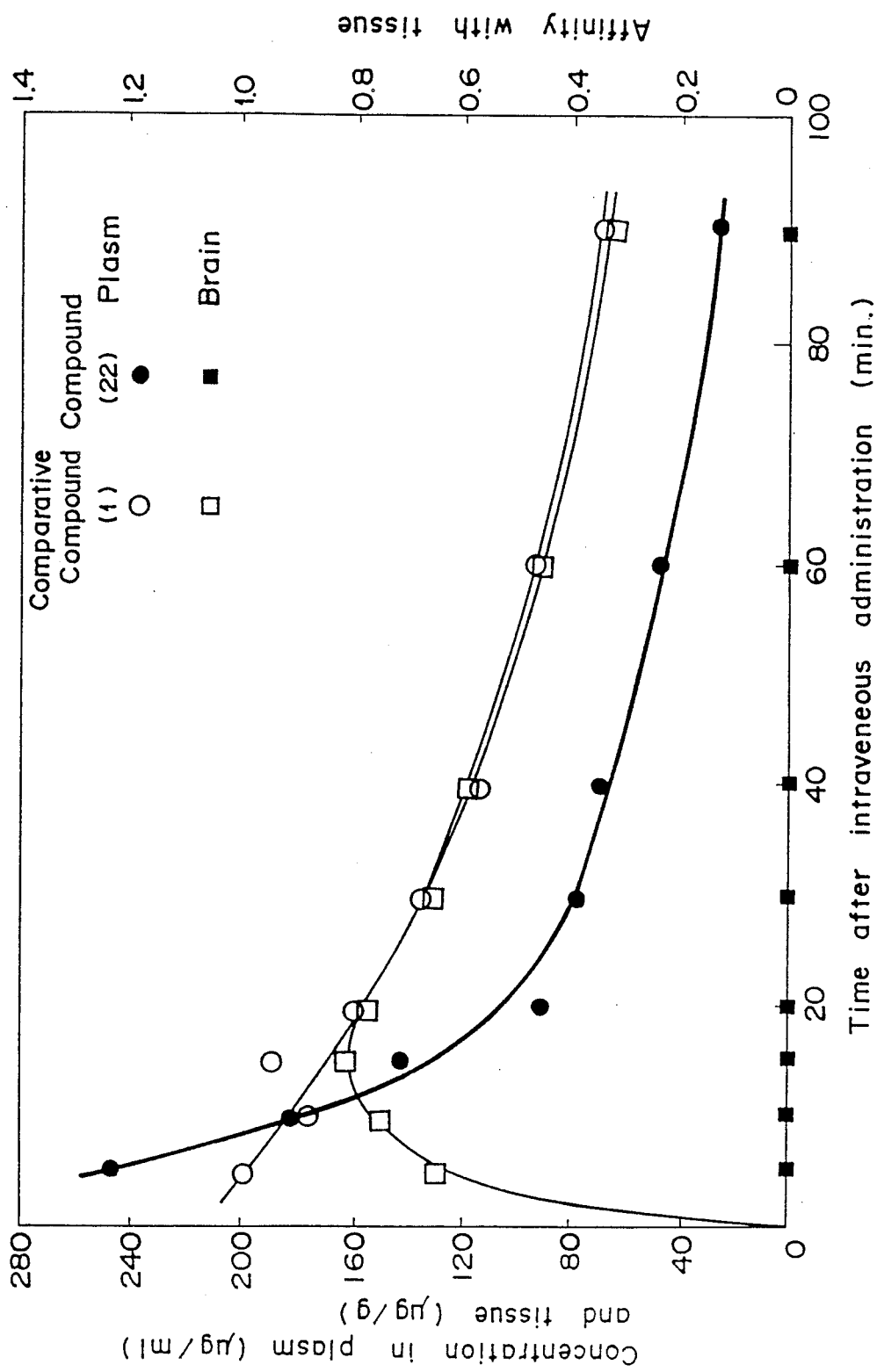
FIG. 1 is a graph showing the relationships between the time after administration of the compounds used in Example 3 and the concentration of the administered compounds in plasm, brain and tumor.

In the nitroimidazole derivative (I) of the present invention, $R_f$ is a group of the formula (II) or (III):

$$-CH_2CFXCH_2OR_1 \qquad (II)$$

wherein X is a hydrogen atom or a halogen atom; $R_1$ is a group of the formula:

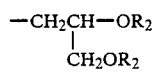

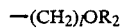

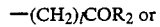

wherein $R_2$ is a hydrogen atom, a hydroxyl group, a $C_1$–$C_3$ alkyl group, a $C_2$–$C_4$ acyl group, benzylidene or acetonide; $R_3$ is a hydrogen atom or a $C_1$–$C_3$ alkyl group; Z is a hydrogen atom, COOY, COOR$_3$, CONHOY, CONR$_4$R$_5$ (wherein R$_4$ and R$_5$ are hydroxyl group-containing $C_1$–$C_3$ alkyl groups or hydrogen atoms; Y is a hydrogen atom or a monovalent metal atom), an amino group, a hydroxy group or OR$_3$; l is an integer of 1 to 3; o is an integer of 0 to 3; p is an integer of 0 to 2; q is an integer of 0 to 3; m and n are integers of 0 to 4; and $1 \leq m+n \leq 4$ or

  (III)

wherein $R_3$, X and p are the same as defined above; Z' is the same as Z or is OCOOCH$_3$; r is an integer of 1 to 3; s is 0 or 1; t is an integer of 0 to 4 provided that when p = 0, s≠0 and at least one X is a fluorine atom.

Preferred examples of the group $R_f$ are as follows:

  (1)

  (2)

-continued

—CH₂CFHCH₂OCH₂CH—O  (3)
         |        \\
         CH₂—O    C(CH₃)₂

—CH₂CF₂CH₂OCH₂CH—O  (4)
         |        \\
         CH₂—O    C(CH₃)₂

—CH₂CFHCH₂OCH₂CHOCOCH₃  (5)
              |
              CH₂OCOCH₃

—CH₂CF₂CH₂OCH₂CHOCOCH₃  (6)
              |
              CH₂OCOCH₃

—CH₂CFHCH₂OCH(CH₂OH)₂  (7)

—CH₂CF₂CH₂OCH(CH₂OH)₂  (8)

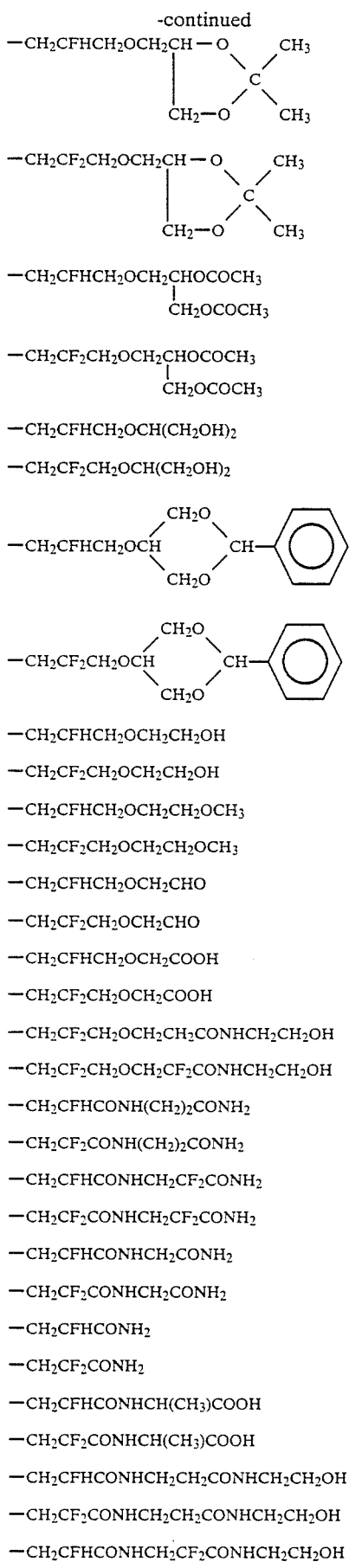

—CH₂CFHCH₂OCH〈CH₂O〉CH—C₆H₅  (9)
             CH₂O

—CH₂CF₂CH₂OCH〈CH₂O〉CH—C₆H₅  (10)
             CH₂O

—CH₂CFHCH₂OCH₂CH₂OH  (11)
—CH₂CF₂CH₂OCH₂CH₂OH  (12)
—CH₂CFHCH₂OCH₂CH₂OCH₃  (13)
—CH₂CF₂CH₂OCH₂CH₂OCH₃  (14)
—CH₂CFHCH₂OCH₂CHO  (15)
—CH₂CF₂CH₂OCH₂CHO  (16)
—CH₂CFHCH₂OCH₂COOH  (17)
—CH₂CF₂CH₂OCH₂COOH  (18)
—CH₂CF₂CH₂OCH₂CH₂CONHCH₂CH₂OH  (19)
—CH₂CF₂CH₂OCH₂CF₂CONHCH₂CH₂OH  (20)
—CH₂CFHCONH(CH₂)₂CONH₂  (21)
—CH₂CF₂CONH(CH₂)₂CONH₂  (22)
—CH₂CFHCONHCH₂CF₂CONH₂  (23)
—CH₂CF₂CONHCH₂CF₂CONH₂  (24)
—CH₂CFHCONHCH₂CONH₂  (25)
—CH₂CF₂CONHCH₂CONH₂  (26)
—CH₂CFHCONH₂  (27)
—CH₂CF₂CONH₂  (28)
—CH₂CFHCONHCH(CH₃)COOH  (29)
—CH₂CF₂CONHCH(CH₃)COOH  (30)
—CH₂CFHCONHCH₂CH₂CONHCH₂CH₂OH  (31)
—CH₂CF₂CONHCH₂CH₂CONHCH₂CH₂OH  (32)
—CH₂CFHCONHCH₂CF₂CONHCH₂CH₂OH  (33)

—CH₂CF₂CONHCH₂CF₂CONHCH₂CH₂OH  (34)
—CH₂CFHCONHCH₂CH₂CON(CH₂CH₂OH)₂  (35)
—CH₂CF₂CONHCH₂CH₂CON(CH₂CH₂OH)₂  (36)
—CH₂CFHCONHCH₂CF₂CON(CH₂CH₂OH)₂  (37)
—CH₂CF₂CONHCH₂CF₂COH(CH₂CH₂OH)₂  (38)
—CH₂CFHCONHCH₂CH₂CONHOY [Y is a  (39)
   hydrogen atom or a monovalent metal atom.]
—CH₂CF₂CONHCH₂CH₂CONHOY [Y is the  (40)
   same as defined above.]
—CH₂CFHCONHCH₂CF₂CONHOY [Y is the  (41)
   same as defined above.]
—CH₂CF₂CONHCH₂CF₂CONHOY [Y is the  (42)
   same as defined above.]
—CH₂CF₂CH₂OCH₂CONHCH₂CH₂OH  (43)
—CH₂CF₂CH₂OCH₂CONHOH  (44)
—CH₂CF₂CH₂OCH₂CF₂CONHCH₂CH₂OH  (45)
—CH₂CF₂CH₂OCH₂CF₂CONH₂  (46)
—CH₂CF₂CONHCH₂CH₂CONHCH₂CH₂OH  (47)
—CH₂CF₂CONHCH₂CONH₂  (48)
—CH₂CF₂CONHCH₂CH₂CH₂OH  (49)
—CH₂CF₂CONH(CH₂)₄OH  (50)
—CH₂CF₂CONHCH₂CH₂OCOOCH₃  (51)
—CH₂CONHCH₂CF₂CONH₂  (52)
—CH₂CHFCH₂OCH₂CF₂CONHCH₂CH₂OH  (53)
—CH₂CHFCH₂OCH₂CONHCH₂CH₂OH  (54)
—CH₂CHFCH₂OCH₂CF₂CONH₂  (55)
—CH₂CHFCH₂OCH₂CONHOH  (56)
—CH₂CF₂CONH(CH₂)₃CONH₂  (57)
—CH₂CF₂CONH(CH₂)₄CONH₂  (58)
—CH₂CF₂CONHCH₂CONHCH₂CH₂OH  (59)
—CH₂CHFCONHCH₂CH₂OCOOCH₃  (60)
—CH₂CHFCONH(CH₂)₄OH  (61)
—CH₂CF₂CH₂OCH₂CF₂CONHOH  (62)
—CH₂CHFCH₂OCH₂CF₂CONHOH  (63)

The nitroimidazole derivative (I) of the present invention may be prepared as follows (hereinafter "NI" means the group of 2-nitroimidazol-1-yl):

(1) An epoxy compound of the formula:

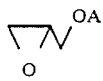

is addition reacted with 2-nitroimdazole to form NI—CH₂—CH(OH)CH₂OA (wherein A is R₁). The reaction temperature is from 0° to 100° C., preferably from 50° to 70° C. Although no solvent is required, the reaction may be carried out in a solvent such as dioxane, tetrahydrofuran (THF) and the like. Then, the hydroxyl group in the compound obtained is fluorinated with a suitable fluorinating agent (e.g. diethylaminosulfatrifluoride (DAST)) to form the present compound (I) in an ether form.

(2) A fluorine-containing α,β-unsaturated carbonyl compound is addition reacted with 2-nitroimidazole to form NI—CH$_2$CHFCOOB (wherein B is an ester-forming group such as methyl or ethyl group).

NI—CH$_2$CF$_2$COOB can be obtained by the reaction of a fluorine-containing oxetane with 2-nitroimidazole in an alcohol solvent such as methanol or ethanol.

(3) An ester NI—CH$_2$CFXCOOB is hydrolyzed and then reduced to form NI—CH$_2$CFXCH$_2$OH. The obtained alcohol compound is reacted with an alkyl halide AX to obtain NI—CH$_2$CFXCH$_2$OA.

The present compound (I) in an amide form can be prepared by reacting NI—CH$_2$CFXCOOA with an amine to form NI—CH$_2$CFXCONDE (wherein D and E are amide-forming groups such as a hydrogen atom and an alkyl group).

The 2-nitroimidazole derivative (I) of the present invention is useful as a radiosensitizer. Its dose depends on the kinds of tumor and/or the compound (I). Generally, it is from 20 to 10,000 mg in case of oral administration, from 0.5 to 10,000 mg in case of injection or 20 to 10,000 mg in case of suppository. An optimum dose may be determined by a medical practitioner according to symptom based on a kind of radiation, a radiation dose, fractionation of irradiation and the like.

The 2-nitroimidazole compound (I) of the present invention may be administered in any suitable form. The compound (I) may be compounded with any carrier which is conventionally used in this field, and formulated by a conventional method.

The present invention is further illustrated by the following Preparation Examples for the 2-nitroimidazole derivatives (I) and Examples showing the radiosensitization effect of the derivatives (I).

PREPARATION EXAMPLE 1

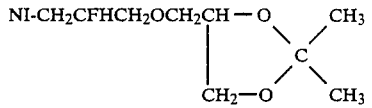 (3)

To a solution of 1,2-O-isopropylideneglycerol (6.0 g, 50 mmol) and epichlorohydrin (18.5 g, 0.2 mol) in dioxane (50 ml), potassium carbonate (2.8 g, 50 mmol) was added and stirred for 3 hours at 70° C. The reaction mixture was filtered and the filtrate was concentrated to obtain 3-O-(2,3-epoxypropyl)-1,2-O-isopropylideneglycerol (6.9 g).

A mixture of the product (4.7 g, 25.2 mmol) and 2-nitroimidazole (1.9 g, 16.8 mmol) was dissolved in ethanol (50 ml). Potassium carbonate (230 mg, 1.7 mmol) was added to the solution and reacted at 70° C. for one hour. After the reaction, the reaction mixture was filtered and the filtrate was concentrated. The residue was taken up in ethyl acetate (100 ml) and washed with water and a saturated sodium chloride solution. The organic phase was dried over magnesium sulfate, concentrated and purified by silica gel column chromatography to obtain 1-(2'-hydroxy-4'-oxa-6',7'-isopropylidenedioxyheptyl)-2-nitroimidazole (3.6 g).

$^1$H-NMR (CDCl$_3$): δ=1.38 (3H, s, —CH$_3$), 1.42 (3H, s, —CH$_3$), 3.58 (4H, m, H$_3$', H$_5$'), 3.72 (1H, dd, J=7 Hz, 8 Hz, H$_7$'a), 4.08 (1H, dd, J=6 Hz, 8 Hz, H$_7$'b), 4.16–4.84 (5H, m, H$_1$', H$_2$', H$_6$', —OH'), 7.07 (1H, s, H$_5$), 7.28 (1H, s, H$_4$).

To 1-(2'-hydroxy-4'-oxa-6',7'-isopropylidenedioxyheptyl)-2-nitroimidazole (3.0 g, 10.0 mmol), dioxane (30 ml) was added and then DAST (2.0 g, 12.4 mmol) was dropwise added while cooling with ice and stirred overnight at a room temperature. The reaction mixture was concentrated and partitioned between ethyl acetate and water. The organic phase was washed with water and dried over magnesium sulfate, concentrated and purified by silica gel column chromatography to obtain 1-(2'-fluoro-4'-oxa-6',7'-isopropylidenedioxyheptyl)-2-nitroimidazole (3) (2.2 g).

$^1$H-NMR (CDCl$_3$)δ=1.39 (3H, s, H$_3$), 1.42 (3H, s, CH$_3$), 3.50–4.80 (9H, m, H$_1$', H$_3$', H$_5$', H$_6$', H$_7$'), 4.60–5.30 (1H, dm, H$_2$'), 7.19 (1H, s, H$_5$), 7.23 (1H, s, H$_4$).

$^{19}$F-NMR (CDCl$_3$; standard: TFA): 113.3.

PREPARATION EXAMPLE 2

 (1)

To 1-(2'-fluoro-4'-oxa-6',7'-isopropylidenedioxyheptyl)-2-nitroimidazole (2.0 g, 6.7 mmol), 1N-HCl (20 ml) and THF (20 ml) were added and stirred for 3 hours at a room temperature. After the reaction, the reaction mixture was concentrated and purified by silica gel column chromatography to obtain 1-(2'-fluoro-4'-oxa-6',7'-dihydroxyheptyl)-2-nitroimidazole (1) (1.0 g).

$^1$H-NMR (DMSO-d$_6$): δ=3.20–3.86 (8H, m, H$_3$', H$_5$', H$_7$', —OH, —OH), 4.40–5.30 (4H, m, H$_1$', H$_2$', H$_6$'), 7.32 (1H, s, H$_5$), 7.78 (1H, s, H$_4$).

$^{19}$F-NMR (DMSO-d$_6$) standard : TFA: 112.9.

PREPARATION EXAMPLE 3

 (15)

To 1-(2'-fluoro-4'-oxa-6',7'-dihydroxyheptyl)-2-nitroimidazole (2.0 g, 7.6 mmol), ethanol (10 ml), water (10 ml) and sodium metaperiodate (1.8 g, 8.4 mmol) were added and stirred for one hour at a room temperature. After the reaction, the reaction mixture was filtered and partitioned between ethyl acetate and water. The organic phase was dried and concentrated to obtain 1-(2'-fluoro-4'-oxa-5'-formylpentyl)-2-nitroimidazole (15) (1.2 g).

PREPARATION EXAMPLE 4

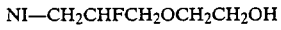 (11)

To a solution of 1-(2'-fluoro-4'-oxa-5'-formylpentyl)-2-nitroimidazole (1.0 g, 4.3 mmol) in methanol (10 ml), sodium borohydride (250 mg, 6.6 mmol) were added while cooling with ice and stirred for one hour. After the reaction, the reaction mixture was acidified by adding 1NHCl. Methanol was distilled off from the mixture. The mixture was extracted with ethyl acetate. The organic phase was washed with water, dried over magnesium sulfate, concentrated and purified by silica gel column chromatography to obtain 1-(2'-fluoro-4'-oxa-6'-hydroxyhexcyl)-2-nitroimidazole (11) (420 mg).

$^1$H-NMR (CDCl$_3$)δ=3.60–4.02 (7H, m, H$_3$', H$_5$', H$_6$', —OH), 4.50–5.02 (2H, m, H$_1$'), 5.08 (1H, dm, J=48 Hz, H$_1$'), 7.18 (1H, s, H$_5$), 7.44 (1H, s, H$_4$).

$^{19}$F-NMR (CDCl$_3$; standard: TFA): 112.8.

PREPARATION EXAMPLE 5

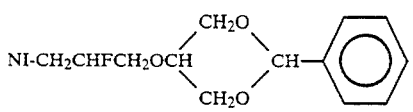 (9)

To a solution of 1,3-O-benzylideneglycerol (5.0 g, 27.8 mmol) and epichlorohydrin (5.1 g, 55.6 mmol) in dioxane (50 ml), potassium hydroxide (2.3 g, 41.7 mmol) was added and stirred for 4 hours at 70° C. The reaction mixture was filtered and the filtrate was concentrated and purified by silica gel column chromatography to obtain 2-O-(2′,3′-epoxypropyl)-1,3-O-benzylideneglycerol (4.2 g).

$^1$H-NMR (CDCl$_3$):δ=2.68 (1H, dd, J=2 Hz, 6 Hz, H$_3$′a), 2,84 (1H, dd, J=3 hz, 6 Hz, H$_3$′b), 3.14–3.34 (1H, m, H$_2$′), 3.40–3.64 (2H, m, H$_1$′), 3.86–4.21 (4H, m, H$_1$, H$_3$), 4.24–4.50 (1H, m, H$_2$), 5.56

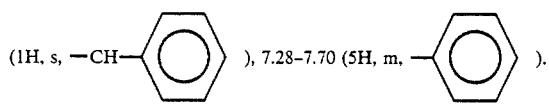

A mixture of the product (3.0 g, 12.7 mmol) and 2 nitroimidazole (1.4 g, 12.7 mmol) was dissolved in ethanol (100 ml). Potassium carbonate (180 mg, 1.3 mmol) was added to the solution and stirred for two hours at 60° C. After the reaction, the reaction mixture was filtered and the filtrate was concentrated. The residue was taken up in ethyl acetate (200 ml) and washed with water and a saturated sodium chloride solution. The organic phase was dried over magnesium sulfate, concentrated and purified by silica gel column chromatography to obtain 1-[3′-(1,3-O-benzylideneglyceroxy)-2′-hydroxypropyl]-2-nitroimidazole (2.10 g).

To the product (2.0 g, 5.7 mmol), dioxane (20 ml) was added and then DAST (1.4 g, 8.6 mmol) was dropwise added while cooling with ice and stirred overnight at a room temperature. After the reaction, excess DAST was decomposed by adding water (5 ml). The reaction mixture was concentrated and partitioned between ethyl acetate and water. Ethyl acetate phase was dried over magnesium sulfate, concentrated and purified by silica gel column chromatography to obtain 1[-3′-(1,3-O-benzilideneglyceroxy)-2′-fluoropropyl]-2-nitroimidazole (9) (1.3 g).

$^1$H-NMR (DMSO-d$_6$): δ=3.30 4.42 (7H, m, H$_3$′, H$_5$′, H$_6$′, H$_1$″), 4.64–5.14 (2H, m, H$_1$′), 5.26 (1H, dm, J=46 Hz, H$_2$′), 7.18–7.60

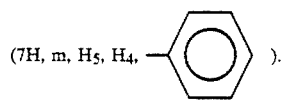

$^{19}$F-NMR (DMSO-d$_6$; standard: TFA): 112.6.

PREPARATION EXAMPLE 6

NI—CH$_2$CHFCH$_2$OCH(CH$_2$OH)$_2$ (7)

To 1-[3′-(1,3-O-benzylideneglyceroxy)-2′-fluoropropyl]-2-nitroimidazole (1.0 g, 2.8 mmol), 1N-HCl (10 ml) and THF (10 ml) were added and stirred for 3 hours at a room temperature. After the reaction, the reaction mixture was concentrated and purified by silica gel column chromatography to obtain 1-[3′-(1,3-dihydroglyceroxy)-2′-fluoropropyl]-2-nitroimidazole (7) (250 mg).

$^1$H-NMR (DMSO-d$_6$): δ=3.32–4.24 (7H, m, H$_3$′, H$_5$′, H$_6$′, H$_1$″), 4.68–5.16 (4H, m, H$_1$′, —OH, —OH), 5.22 (dm, 1H, J=46 Hz), 7.20 (1H, s, H$_5$), 7.46 (1H, s, H$_4$).

$^{19}$F-NMR (DMSO-d$_6$; standard TFA) 112.2.

PREPARATION EXAMPLE 7

NI—CH$_2$CF$_2$CONH$_2$ (28)

To methyl 3-(2′-nitroimidazolyl)-2,2-difluoropropionate (5.00 g, 21.3 mmol), 10% ammonia solution (80 ml) in methanol was added and stirred for 3 hours at a room temperature. Then, the reaction mixture was concentrated. Methanol (100 ml) was added to the concentrate and throughly stirred. Insoluble fraction was filtered off. The filtrate was concentrated, subjected to silica gel column chromatography and recrystallized from ethanol to obtain 3-(2′-nitroimidazolyl)-2,2-difluoropropionic acid amide (2.57 mg). m.p. 149.5°–151.5° C.

$^1$H-NMR (DMSO-d$_6$): δ=5.40 (2H, t, H$_3$, J$_{H3—F}$=15 Hz), 7.41 (1H, d, H$_4$′, J$_{H4'—H5'}$=1 Hz), 7.82 (1H, d, H$_5$′, J$_{H5'—H4'}$), 8.36 (1H, bs, —NH$_2$), 8.56 (1H, bs, —NH$_2$)

$^{19}$F-NMR (DMSO-d$_6$; standard: TFA): 30.9

PREPARATION EXAMPLE 8

NI—CH$_2$CF$_2$CONHCH$_2$CH$_2$CONH$_2$ (22)

To a heterogeneous system of methyl 3-(2′-nitroimidazolyl)-2,2-difluoropronionate (5.00 g, 21.3 mmol) and β-alanine methyl ester hydrochloride (5.10 g, 36.5 mmol) in methanol (50 ml), potassium hydroxide powder (4.6 g, 82 mmol) was gradually added while stirring. Then, the reaction mixture was further stirred for one hour at a room temperature. The reaction solution was filtered with using a Kiriyama funnel and the filtrate was concentrated and partitioned between chloroform and water. The organic phase was dried over magnesium sulfate, filtered and concentrated. Ten % ammonia methanol solution (40 ml) was added to the residue, stirred for two days at a room temperature and then concentrated. The concentrate was subjected to silica gel column chromatography and recrystallized from a mixed solvent of chloroform/methanol to obtain 3-[3′-(2″-nitroimidazolyl)-2′,2′-difluoropropionylamino]propionic acid amide (3.50 g). m.p. 158.0°–160.0° C.

$^1$H-NMR (DMSO—d$_6$): δ=2.42 (2H, t, —CH$_2$CO, J=1 Hz), 3.31–3.60 (2H, m, —NHCH$_2$—), 5.39 (2H, t, —CH$_2$CF$_2$—, J =15 Hz), 7.02 (1H, bs, —CONH$_2$), 7.40 (1H, d, H$_5$″, J$_{H5''—H4''}$=1 Hz), 7.52 (1H, bs, —CONH$_2$), 7.80 (1H, d, H$_4$″, J$_{H4''—H541}$ =1 Hz), 9.16 (1H, t, —CONH—, J=6 Hz).

$^{19}$F—NMR (DMSO-d$_6$; standard: TFA): 31.2.

PREPARATION EXAMPLE 9

NI—CH$_2$CF$_2$CONHCH$_2$CF$_2$CONH$_2$ (24)

To a solution of methyl 3-(2′-nitroimidazolyl)-2,2-difluoropropionate (10.0 g, 42.5 mmol) in methanol (60 ml), 2,2-difluoro-3-amino-propionic acid amide (10.4 g, 83.8 mmol) was added and reacted for 20 hours at room temperature while stirring. Then, insoluble fraction was filtered off from the reaction mixture. The filtrate was concentrated, subjected to silica gel column chromatography and recrystallized from ethanol to obtain 3-[3'-(2''-nitroimidazolyl)-2',2'-difluoropropionylamino]-2,2-difluoropropionic acid amide (4.98 g). m.p. 134.5°–135.5° C.

$^1$H-NMR (DMSO-d$_6$): δ=3.95 (2H, dt, H$_3$, $J_{H3'-F}$=15 Hz), 7.44 (1H, s, H$_4''$), 7.83 (1H, s, H$_5''$), 8.20 (1H, bs, —NH$_2$), 8.42 (1H, bs, NH$_2$), 9.63 (1H, bt, —CONH—, $J_{NH-H3}$ =6 Hz).

$^{19}$F-NMR (DMSO-d$_6$; standard: TFA): 30.9, 31.6.

PREPARATION EXAMPLE 10

NI—CH$_2$CF$_2$CH$_2$OCH$_2$CONHCH$_2$CH$_2$OH (43)

To a suspension of sodium hydride (500 mg, 20.8 mmol) in dry THF (20 ml) which was cooled at −50° C., a solution of 3-(2'-nitroimidazolyl)-2,2-difluoropropanol (2.0 g, 9.6 mmol) in dry THF (10 ml) and then a solution of ethyl bromoacetate (2.4 g, 14.4 mmol) in dry THF were dropwise added. Then, the reaction mixture was gradually warmed to a room temperature and stirred for 4 hours at the temperature. After the reaction, the mixture was cooled by ice. Ethanol (2 ml) was added to the mixture, concentrated and partitioned between ethyl acetate and water. The organic phase was dried over magnesium sulfate, filtered, concentrated and purified by silica gel column chromatography to obtain ethyl 2-[3'-(2''-nitroimidazolyl)-2',2'-difluoropropoxy]acetate (2.4 g)

The product (1.0 g, 3.4 mmol) was dissolved in dioxane (10 ml). To the solution, ethanolamine (600 mg, 9.8 mmol) was added and heated for 9 hours under reflux with stirring. The reaction solution was concentrated and partitioned between ethyl acetate and water. The organic phase was dried over magnesium sulfate, filtered, concentrated and subjected to silica gel column chromatography to obtain 2[3'-(2''-nitroimidazolyl)-2',2'-difluoropropoxy]acetic acid hydroxyethylamide (280 mg).

$^1$H-NMR (DMSO-d$_6$): δ=3.20–3.80 (5H, m), 4.08 (2H, t, —CF$_2$CH$_2$—, J=14 Hz), 4.17 (2H, s, —CH$_2$CO), 5.32 (2H, t, —CH$_2$CF$_2$, J=15 Hz), 7.40 (1H, d, H$_5''$), 7.83 (1H, d, H$_4''$), 7.90 (1H, bt, NH).

$^{19}$F-NMR (DMSO-d$_6$; standard: TFA): 30.9.

PREPARATION EXAMPLE 11

NI—CH$_2$CF$_2$CH$_2$OCH$_2$CONHOH (44)

To sodium methoxide (28% solution in methanol; 3.9 g), methanol (10 ml) and then hydroxylamine hydrochloride (2.0 g, 28.8 mmol) were added and stirred for 2 hours at a room temperature. Then, the reaction mixture was filtered. To the filtrate, ethyl 2-[3'-(2''-nitroimidazolyl)-2',2'-difluoropropoxy]acetate (600 mg, 2.0 mmol) was added and heated for 12 hours under reflux with stirring. The reaction solution was concentrated and partitioned between ethyl acetate and water. The organic phase was dried over magnesium sulfate, filtered, concentrated and purified by silica gel column chromatography to obtain 2-[3'-(2''nitroimidazolyl-2',2'-difluoropropoxylacetic acid hydroxyamide (200 mg). m.p. 67°–68° C.

$^1$H-NMR (DMSO-d$_6$): δ=4.08 (2H, t, —CF$_2$CH$_2$—, J=14 Hz), 4.17 (2H, s, CH$_2$CO), 5.34 (2H, t, —CH$_2$C-

F$_2$—, J=15 Hz), 7.44 (1H, d, H$_5''$), 7.84 (1H, d, H$_4''$), 9.14 (1H, bs, NH).

$^{19}$F-NMR (DMSO-d$_6$; standard: TFA): 31.3.

PREPARATION EXAMPLE 12

NI-CH$_2$CF$_2$CH$_2$OCH$_2$CF$_2$CONHCH$_2$CH$_2$OH (45)

To a solution of methyl 3-[3'-(2''-nitroimidazolyl)-2',2'-difluoropropoxy]-2,2-difluoropropionate (1.0 g, 3.0 mmol) in dioxane (10 ml), ethanolamine (370 mg, 6.0 mmol) was added and reacted for 5 hours at a room temperature with stirring. The reaction solution was concentrated and partitioned between ethyl acetate and water. The ethyl acetate phase was dried over magnesium sulfate, filtered, concentrated and purified by silica gel column chromatography to obtain 3-[3'-(2''-nitroimidazolyl)-2',2'-difluoropropoxy]-2,2-difluoropropionic acid hydroxyethylamide (550 mg). m.p. 67°–68° C. $^1$H-NMR (DMSO-d6): δ=3.24–3.76 (5H, m), 4.14 (2H, t, —CF$_2$CH$_2$—, J=13 Hz), 4.22 (2H, t, —OCH$_2$, J=14 Hz), 4.88 (1H, brt, —OH), 5.24 (2H, t, CH$_2$CF$_2$, J=15 Hz), 7.42 (1H, d, H$_5''$), 7.98 (1H, d, H$_4''$), 8.93 (1H, brt, NH)

$^{19}$F-NMR (DMSO-d$_6$; standard: TFA): 31.6, 34.6.

PREPARATION EXAMPLE 13

NI—CH$_2$CF$_2$CH$_2$OCH$_2$CF$_2$CONH$_2$ (46)

To a suspension of sodium hydride (700 mg, 29.2 mmol) in dry THF (50 ml) which was cooled to −30° C., a solution of 3-(2'-nitroimidazolyl)-2,2-difluoropropanol (5.0 g, 24.0 mmol) in dry THF (10 ml) and then a solution of tetrafluorooxatane (15.6 g, 120 mmol) in dry THF were dropwise added. Then, the reaction mixture was gradually warmed to a room temperature and stirred for 3 hours at the temperature. After the reaction, the reaction mixture was cooled by ice. To the mixture, methanol (5 ml) was slowly added. The reaction solution was concentrated and partitioned between ethyl acetate and water. The organic phase was dried over magnesium sulfate, filtered, concentrated and purified by silica gel column chromatography to obtain methyl 3-[3'-(2''-nitroimidazolyl)-2',2'-difluoropropoxy]-2,2-difluoropropionate (2.2 g).

To the product (1.0 g, 3.0 mmol), 15 % ammonia methanol solution (50 ml) was added and stirred for 10 hours at a room temperature. The reaction solution was concentrated and purified by silica gel column chromatography to obtain 3-[3'-(2''-nitroimidazolyl)-2',2'-difluoropropoxy]2,2-difluoropropionylamide (400 mg). m.p. 86°–87° C.

$^1$H-NMR (DMSO-d$_6$): δ=4.20 (2H, t, CF$_2$CH$_2$, J=13 Hz), 4.24 (2H, t, —OCH$_2$, J=14 Hz), 5.28 (2H, t, —CH$_2$CF$_2$, J =15 Hz), 7.45 (1H, d, H$_5''$), 7.84 (1H, d, H$_4''$), 8.24 (1H, bs, NH$_2$), 8.44 (1H, bs, NH$_2$).

$^{19}$F-NMR (DMSO-d$_6$; standard: TFA): 31.5, 34.4.

PREPARATION EXAMPLE 14

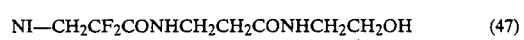
NI—CH$_2$CF$_2$CONHCH$_2$CH$_2$CONHCH$_2$CH$_2$OH (47)

To a solution of methyl 3-(2'-nitroimidazolyl)-2,2-difluoropropionate (10.0 g, 42.4 mmol) in methanol (50 ml), β-alanine methyl ester (8.38 g, 81.3 mmol) was added and stirred for one hour at a room temperature. Then, the reaction solution was concentrated and partitioned between ethyl acetate and a saturated sodium chloride solution. The organic phase was dried over magnesium sulfate, filtrated and concentrated.

To the residue, dioxane (25 ml) and then ethanolamine (3.5 ml, 58.0 mmol) were added and heated for 4 hours under reflux. After the reaction, the solution was concentrated and partitioned between ethyl acetate and a saturated sodium chloride solution. The organic phase was dried over magnesium sulfate and filtered. The filtrate was concentrated and purified by silica gel column chromatography to obtain 3-[3'-(2''-nitroimidazolyl)-2',2'-difluoropropionamido]propionic acid hydroxyethylamide (1.2 g).

$^1$H-NMR (DMSO-d$_6$): δ=2.44 (2H, t, —CH$_2$CO), 3.12–3.64 (6H, s), 4.79 (1H, t, —OH, J=5.7 Hz), 5.38 (1H, t, H$_3$', J=14.8 Hz), 7.40 (1H, d, H$_5$''), 7.80 (1H, d, H$_4$''), 8.05 (1H, brt, —CH$_2$CONH, J=5.8 Hz), 9.16 (1H, brt, —CF$_2$CONH, J=5.8 Hz).

$^{19}$F-NMR (DMSO-d$_6$; standard: TFA): 31.2.

PREPARATION EXAMPLE 15

NI—CH$_2$CF$_2$CONHCH$_2$CONH$_2$ (48)

To a solution of methyl 3-(2'-nitroimidazolyl)-2,2-difluoropropionate (10.0 g, 42.4 mmol) in methanol (30 ml), a solution of glycineamide (5.0 g, 67.6 mmol) in methanol was dropwise added and stirred for 30 minutes at a room temperature. Then, the insoluble fraction was collected by filtration and recrystallized from methanol to obtain 2-[3'-(-(2''-nitroimidazolyl)-2',2'-difluoropropionamido]ethylamide (4.42 g). m.p. 183.5°–185.0° C.

$^1$H-NMR (DMSO-d$_6$): δ=3.79 (2H, d, —CH$_2$CO—, J$_{H2-NH}$=6.0 Hz), 5.35 (2H, t, —CH$_2$CF$_2$—, J$_{H3'-F}$=15.0 Hz), 7.21 ($^1$H, bs, —NH$_2$), 7.34 (1H, d, H$_5$''), 7.53 (1H, bs, —NH$_2$), 7.78 (1H, d, H$_4$''), 9.21 (1H, brt, —NH—, J$_{NH-H2}$=6.0 Hz).

$^{19}$F-NMR (DMSO-d$_6$; standard TFA): 31.4.

PREPARATION EXAMPLE 16

NI—CH$_2$CF$_2$CONHCH$_2$CH$_2$CH$_2$OH (49)

To a solution of methyl 3-(2'-nitroimidazolyl)-2,2-difluoropropionate (2.0 g, 8.5 mmol) in dioxane (10 ml), n-propanolamine (1.0 g, 13.3 mmol) was added and stirred for 2 hours at 70 ° C. Then, the reaction solution was concentrated and partitioned between ethyl acetate and water. The organic phase was dried over magnesium sulfate, filtered, concentrated and subjected to silica gel column chromatography to obtain.3-(2'-nitroimidazolyl)-2,2-difluoropropionic acid hydroxypropylamide (1.7 g).

$^1$H-NMR (DMSO-d$_6$): δ=1.76 (2H, quint, J=6 Hz, CH$_2$), 3.34 (2H, m, —CH$_2$OH), 3.46–3.76 (2H, m, NHCH$_2$), 4.68 (1H, t, —OH), 7.46, 7.86 (each 1H, d, H$_5$', H$_4$'), 9.18 (1H, brt, NH).

$^{19}$F-NMR (DMSO-d$_6$; standard: TFA): 31.1.

PREPARATION EXAMPLE 17

NI—CH$_2$CF$_2$CONH(CH$_2$)$_4$OH (50)

To a solution of methyl 3-(2'-nitroimidazolyl)-2,2-difluoropropionate (1.0 g, 4.2 mmol) in DMF (10 ml), n-butanolamine (500 mg, 5.6 mmol) was added and stirred for 6 hours at a room temperature. Then, the reaction solution was concentrated and purified by silica gel column chromatography to obtain 3-(2'-nitroimidazolyl)-2,2-difluoropropionic acid hydroxybutylamide (450 mg).

$^1$H-NMR (DMSO-d$_6$): δ=1.40–1.80 (4H, m), 3.16–3.44 (2H, m), 3.48–3.70 (2H, m), 4.62 (1H, t, —OH), 5.42 (2H, t, CH$_2$CF$_2$, J=14 Hz), 7.42 (1H, d, H$_5$'), 7.82 (1H, d, H$_4$'), 9.18 (1H, bt, NH).

$^{19}$F-NMR (DMSO-d$_6$; standard: TFA): 31.0.

PREPARATION EXAMPLE 18

NI—CH$_2$CF$_2$CONHCH$_2$CH$_2$OCOOCH$_3$ (51)

3-(2'-Nitroimidazolyl)-2,2-difluoropropionic acid hydroxyethylamide (6.0 g, 22.7 mmol) was dissolved in a solvent mixture of methyl chloroformate (30 ml) and chloroform (30 ml) and cooled by ice. To the solution, a solution of pyridine (6.0 ml) in chloroform (30 ml) was dropwise added over 2 hours. The completion of the reaction was confirmed by thin-layer chromatography. Then, the reaction solution was washed with dilute hydrochloric acid and water, dried over magnesium sulfate, concentrated and subjected to silica gel column chromatography to obtain methyl 3-(2'-nitroimidazolyl)-2,2-difluoropropionamidoethoxyformate (6.89 g). m.p. 50.5°–52.5° C.

$^1$H-NMR (DMSO-d$_6$): δ=3.56 (2H, dt, J=5.7 Hz, NHCH$_2$), 3.86 (3H, s, —CH$_3$), 4.50 (2H, t, J=5.7 Hz, —CH$_2$CO—), 5.38 (2H, t, J=14.8 Hz, —CH$_2$CF$_2$—), 7.40 (1H, d, H$_5$'), 7.78 (1H, d, H$_4$'), 9.42 (1H, bt, —CONH—).

$^{19}$F-NMR (DMSO-d$_6$; standard: TFA): 31.1.

PREPARATION EXAMPLE 19

NI—CH$_2$CONHCH$_2$CF$_2$CONH$_2$ (52)

A solution of ethyl 2-(2'-nitroimidazolyl)acetate (2.0 g, 10.1 mmol) and difluoro-β-alanineamide (2.5 g, 20.2 mmol) in methanol (10 ml) was heated for 10 hours under reflux. Then, the reaction solution was concentrated and partitioned between ethyl acetate and water. The aqueous phase was concentrated and subjected to silica gel column chromatography to obtain 3-[2'-(2''-nitroimidazolyl)acetoamido]-2,2-difluoropropionic acid amide (200 mg).

$^1$H-NMR (DMSO-d$_6$): δ=3.20 (2H, t, J=16 Hz, —CH$_2$CF$_2$—), 5.24 (2H, s, CH$_2$CO), 7.38 (1H, d, H$_5$''), 7.80 (1H, d, H$_4$''), 7.44–8.50 (3H, m, NH, NH$_2$).

$^{19}$F-NMR (DMSO-d$_6$; standard: TFA): 33.4.

EXAMPLE 1

Radiosensitization effect on cells (ER in vitro)

To examine the the in vitro radiosensitization effect of the present 2-nitroimidazole derivative (I), 100,000 cells of Chinese hamster V-79 cells were cultured in monolayer in a culture dish, and the V-79 cells in a log phase were prepared.

A solution of a predetermined concentration (1.0 mM) of a compound to be examined in a medium was added to the dish. After standing for 60 minutes at 37° C., the dish was placed in a closed vessel at room temperature. Then, the vessel was purged with nitrogen for 10 minutes to exclude oxygen and X-ray was irradiated at a dose rate of 1.6 Gy/min.

After the irradiation, the cells were washed with phosphate buffer and digested with trypsin into single cells. Then, a predetermined amount of the cells was introduced into 5 ml of a culture medium in a culture dish and cultured for 7 days at 37° C. After staining and washing with water, the number of colonies formed was counted.

The results are shown in following Table 1 as ER in vitro.

For comparison, the irradiation was carried out in the nitrogen atmosphere or in the air after adding the medium without the test compound.

EXAMPLE 2

Radiosensitization effect on tumor transplanted in animal (ER in vivo)

To both thighs of male Bal/c mouse (8 weeks; 4 mice in a group), $10^5$ of EMT-6 tumor cells were subcutaneously inoculated. After the diameter of the tumor reached about 1 cm, a solution of a compound to be examined in saline in an amount of 100 mg of the compound per kg was intraperitonealy administered. After 40 minutes, X-ray was irradiated at 450 rad/min. for 5 minutes and then the mouse was sacrificed.

After the whol body of the mouse was sterilized with 70% ethanol, the tumor was taken out. The tissue was homogenized and then digested by stirring for 50 minutes at 37° C. with adding 22 ml of trypsin. The number of cells in the supernatant was counted. A predetermined amount of the cells was introduced in a plastic plate having a diameter of about 5 cm. To the plate, 5 ml of medium was added and cultured in a $CO_2$ incubator. The plate containing the irradiated cells was removed from the incubator after 9 days, while a comparison dish containing unirradiated cells was incubated for 10 days. The cells were fixed by methanol and strained by Giemsa stain. Then, the number of colonies formed were counted.

The survival rate was calculated with using the data of the unirradiated cells as control. The results are shown as ER in vivo in following Table 1.

TABLE 1

| Rf | ER in vitro | ER in vivo | $LD_{50}$ (mg/kg)*2 |
|---|---|---|---|
| (1) | 1.49 | 1.38 | 2700 |
| (11) | 1.66 | 1.52 | — |
| (22) | 1.46 | 1.58 | 2800 |
| (24) | 1.76 | 1.41 | 2600 |
| (28) | 1.48 | 1.32 | 1100 |
| (43) | 1.54 | 1.38 | >2000 |
| (44) | 1.68 | 1.48 | |
| (45) | 1.63 | 1.40 | >1600 |
| (46) | 1.58 | 1.45 | |
| (47) | 1.43 | 1.38 | >2000 |
| (48) | 1.61 | 1.49 | 2200 |
| (51) | | | >3000 |
| Comparative (1)*1 | 1.50 | 1.43 | 1200 |

Note:
*1 Misonidazole [Rf = —CH₂CH(OH)—CH₂OCH₃] was used for comparison.
*2 For determination of $LD_{50}$, female ICR mice of 5 weeks were used.

EXAMPLE 3

Distribution of the radiosensitizer in a mouse body

To a right thigh of each of eight female C3H mice (8 weeks), SCO VII tumor cells were subcutaneously inoculated. After about two weeks at which the tumor reached 10 mm, a solution of a compound to be examined in saline at a predetermined concentration was intravenously administered (for example, 200 mg of the compound per kg). After 5, 10, 15, 20, 30, 40, 60 and 90 minutes from the administration, an amount of blood was sampled from the eye socket and then the mice were sacrificed. The tumor and the brain were taken out and weighed. They were homogenized in 10 time volume of pure water. Then, to the homogenate, methanol of two time volume of the homogenate was added and thoroughly stirred followed by centrifugation. The supernatant was analyzed with liquid chromatography to find the distribution of the compound in each organ. The results for the compound (22) and the comparative compound (1) are shown in FIG. 1.

It has been shown that the present compounds have less tendency to pass the blood-brain barrier and therefore is less neurotoxic than the compounds disclosed in Japanese Patent Kokai Publication No. 20456/1988.

What is claimed is:

1. A 2-nitroimidazol derivative of the formula:

wherein $R_f$ is a group of the following formula (II) or (III):

wherein X is a hydrogen atom or a halogen atom; $R_1$ is a group of the formula:

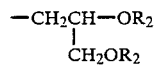

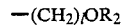

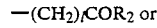

wherein $R_2$ is a hydrogen atom, a hydroxyl group, a $C_1$–$C_3$ alkyl group, a $C_2$–$C_4$ acyl group, benzylidene or acetonide; $R_3$ is a hydrogen atom or a $C_1$–$C_3$ alkyl group; Z is a hydrogen atom, COOY, COOR₃, CONHOY, CONR₄R₅ (wherein R₄ and R₅ are hydroxyl group-containing $C_1$–$C_3$ alkyl groups or hydrogen atoms; Y is a hydrogen atom or a monovalent metal atom), an amino group, a hydroxyl group or OR₃; is an integer of 1 to 3; o is an integer of 0 to 3; p is an integer of 0 to 2; q is an integer of 0 to 3; m and n are integers of 0 to 4; and $1 \leq m+n \leq 4$ or

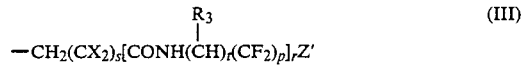

wherein R₃, X and p are the same as defined above; Z' is the same as Z or is OCOOCH₃; r is an integer of 1 to 3; s is 0 or 1; t is an integer of 0 to 4 provided that when p=0, s≠0 and at least one X is a fluorine atom.

* * * * *